(12) United States Patent
Goedert et al.

(10) Patent No.: US 6,245,575 B1
(45) Date of Patent: Jun. 12, 2001

(54) SCREENING OF AGENTS FOR TREATMENT OF ALZHEIMER'S DISEASE

(75) Inventors: Michel Goedert; Ross Jakes; Maria Grazia Spillantini; Masato Hasegawa; Michael John Smith; Richard Anthony Crowther, all of Cambridge (GB)

(73) Assignee: Medical Research Council, London (GB)

( * ) Notice: Subject to any disclaimer, the term of this patent is extended or adjusted under 35 U.S.C. 154(b) by 0 days.

(21) Appl. No.: 09/194,127

(22) PCT Filed: May 20, 1997

(86) PCT No.: PCT/GB97/01356

§ 371 Date: Jul. 16, 1999

§ 102(e) Date: Jul. 16, 1999

(87) PCT Pub. No.: WO97/44669

PCT Pub. Date: Nov. 27, 1997

(30) Foreign Application Priority Data

May 23, 1996 (GB) ................................. 96108295

(51) Int. Cl.$^7$ .................................... G01N 33/00

(52) U.S. Cl. ................ 436/86; 436/87; 436/89; 436/95; 435/105; 435/106

(58) Field of Search .................. 436/86, 87, 89, 436/95; 435/106, 105

(56) References Cited

U.S. PATENT DOCUMENTS 5,164,295 * 11/1992 Kisilevsky et al. .................. 435/7.8
5,643,562 * 7/1997 Kisilevsky et al. ............... 424/78.31

(List continued on next page.)

FOREIGN PATENT DOCUMENTS 93 10459   5/1993 (WO).
93 11231   6/1993 (WO).

OTHER PUBLICATIONS

Su et al. "Localization of heparan sulfate glycosaminoglycan and proteoglycan core protein in aged brain and Alzheimer's disease", abstract 1992.*

Yang et al. "Protein kinase Fa/glycogen synthase kinase–3alpha after heparin potentiation phosphorylates tau on sites abnormally phosphorylated in Alzheimer's Disease brain", J. Neurochem. (1994), 63 (4), 1416–25.*

Song et al. "Tau protein kinase I/GSK–3 beta/kinase FA in heparin phosphorylatesd tau on Ser199, Thr231, Ser235, Ser262, Ser369 and Ser400 sites phosphorylated in Alshemer disease brain", abstract, 1995.*

(List continued on next page.)

Primary Examiner—Jill Warden
Assistant Examiner—Yelena Gakh
(74) Attorney, Agent, or Firm—Pillsbury Winthrop LLP

(57) ABSTRACT

A method of screening an agent for potential use in the treatment of Alzheimer's disease, comprises reacting, in the presence of the agent, tau protein with a suitable sulphated carbohydrate under appropriate conditions to form filaments, and monitoring for the presence of filaments. Tau protein and sulphated carbohydrate, e.g. sulphated glycosaminoglycan, will react under appropriate conditions to form filaments, either paired helical filaments or straight filaments. If filament formation is affected when the reaction is carried out in the presence of an agent being screened, this is possibly due to an interfering, inhibiting or blocking effect of the agent. An agent which inhibits assembly of PHFs in vitro may also have an inhibiting effect in vivo and thus have potential therapeutic value in delaying the dementing effects of Alzheimer's disease. The invention can thus provide a screen to identify agents worthy of further investigation for use in the treatment of Alzheimer's disease.

7 Claims, 4 Drawing Sheets

U.S. PATENT DOCUMENTS 5,728,375 * 3/1998 Kisilevsky et al. ............... 424/78.31
5,840,294 * 11/1998 Kisilevsky et al. ............... 424/78.31

OTHER PUBLICATIONS

Goedert et al. "Multiple isoforms of human microtubule–associated protein tau: sequences and localization in neurofibrillary tangles of Alzheimer's disease", Neuron (1989), 3(4), 519–26.*

Moreno et al: "Glysogen synthase kinase 3 phosphorylates recombinant human tau protein at serine–262 in the presence of heparin (or tubulin)" FEBS LETTERS., vol. 372, No. 1, Sep. 18, 1995, pp. 65–68, XP002041922.

Chemical Abstract, vol. 121, No. 17, Oct. 24, 1994, abstract No. 202384, Yang et al: "Protein kinase Fa/glycogen synthase kinases–3–alpha after heparin potentiation phosphorylates tau on sites abnormally phosphorylated in Alzheimer's disease brain", p. 879, col 2, XPOOSO41923.

* cited by examiner

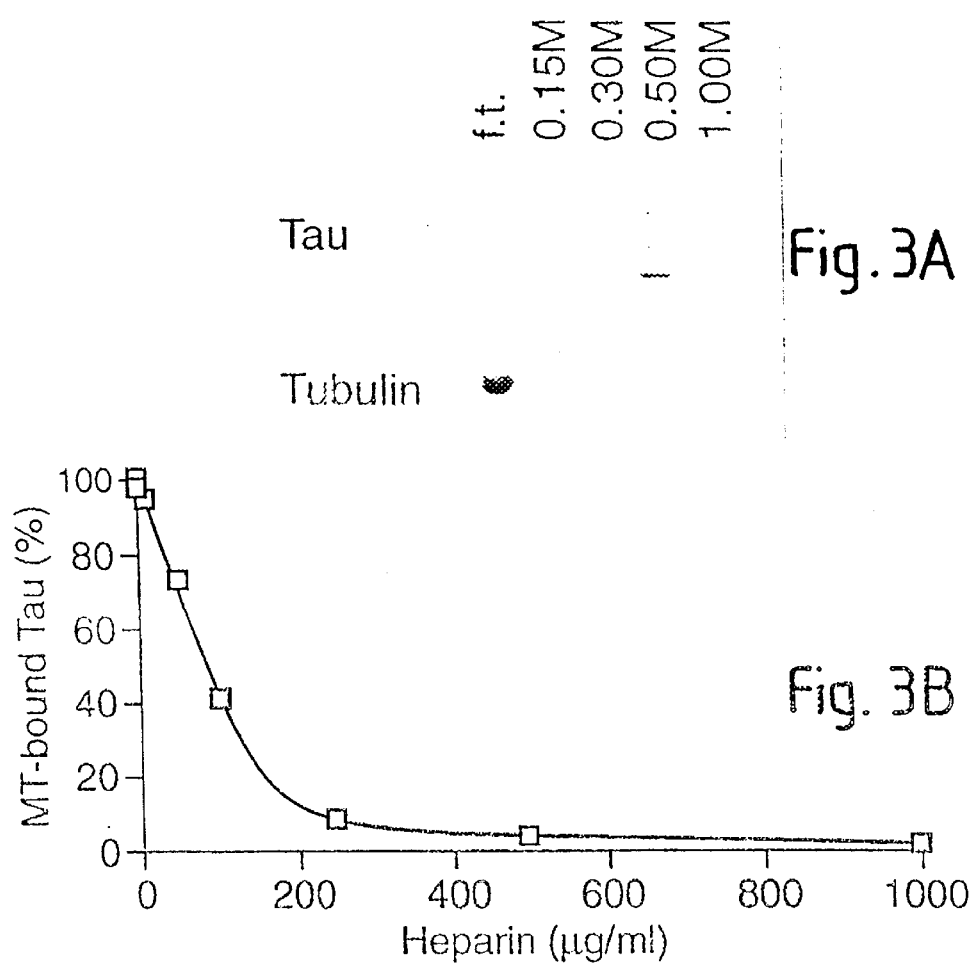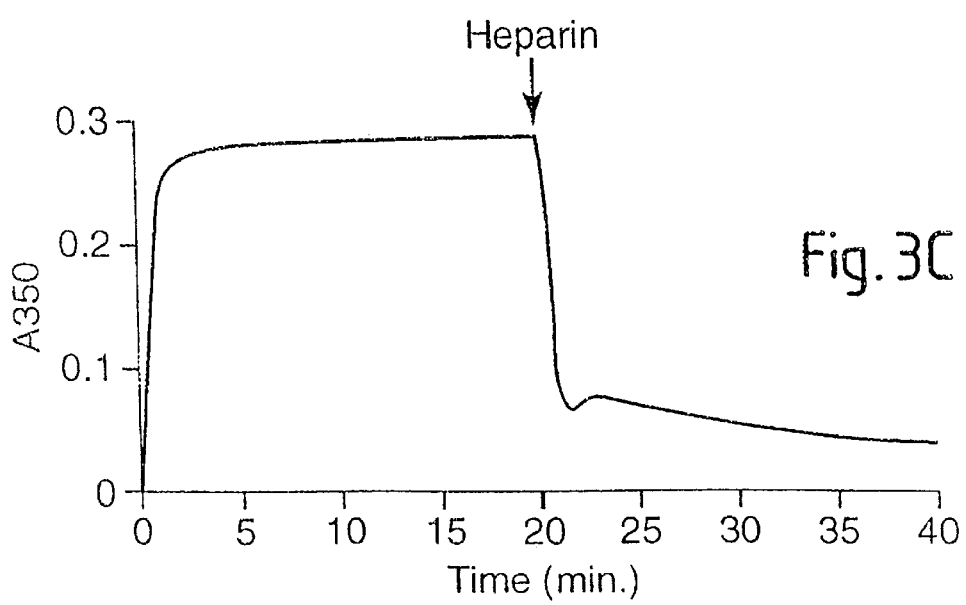

SCREENING OF AGENTS FOR TREATMENT OF ALZHEIMER'S DISEASE

This application is the national phase of international application PCT/GB97/01356 filed May 20, 1997 which designated the U.S.

FIELD OF THE INVENTION

This invention concerns screening agents for treatment of Alzheimer's disease, and concerns a method of screening an agent for potential use in the treatment of Alzheimer's disease.

BACKGROUND TO THE INVENTION

Alzheimer's disease is the leading cause of dementia in the elderly. The brains of patients with Alzheimer's disease contain characteristic structural lesions known as plaques and tangles. Plaques will not be considered here. Neurofibrillary tangles represent intracellular accumulations of paired helical filaments (PHFs), which are quite unlike any of the normal structural elements of the neuronal cytoskeleton. Tangles become extracellular on the death of the affected cell. PHFs are also found in abnormal neurites associated with neuritic plaques and as an extensive distribution of fine neurophil threads throughout affected regions of the brain. The extent of neurofibrillary degeneration found post mortem appears to provide the most reliable pathological correlate of the degree of dementia observed in life. These topics are discussed further in references 1 and 2.

PHFs are made of microtubule-associated protein tau in a hyperphosphorylated state (3–8). Hyperphosphorylation of tau is known to result in its inability to bind to microtubules (9, 10) and is believed to precede PHF assembly (11). However, it is unclear whether hyperphosphorylation of tau is either necessary or sufficient for PHF formation. A major reason for this lack of understanding is that it has not hitherto been possible to form paired helical-like filaments for full-length tau protein either in vitro or in vivo.

Tau protein consists in adult human brain of six isoforms, produced from a single gene by alternative mRNA splicing. The isoforms, which range in size from 352 to 441 amino acids, contain towards the carboxyl terminus a tandem repeat region with three or four homologous stretches of 31 or 32 amino acids. The other isoforms are generated by the presence of a 29- or 58- amino-acid insertion in the amino-terminal half of the protein.

The repeat region of tau represents the microtubule-binding domain, and the amino-terminal half of the protein appears to form an arm-like projection from the surface of the microtubule.

When tau protein is in hyperphosphorylated state (PHF-tau) the protein is unable to bind to microtubules and assembles into PHFs or structural variants known as straight filaments (SFs). The repeat region of tau constitutes the core of the resulting filaments.

See references 31 and 32 for further discussion of tau protein.

The present invention is based on the discovery that suitable sulphated carbohydrates can induce in vitro assembly of tau protein into filaments like those in Alzheimer's disease under physiological conditions in an essentially quantitative manner. This discovery forms the basis of an in vitro assay or screen for agents that inhibit the assembly and so may have potential use in the treatment of Alzheimer's disease.

SUMMARY OF THE INVENTION

The present invention thus provides a method of screening an a gent for potential use in the treatment of Alzheimer's disease, comprising reacting, in the presence of the agent, tau protein with a suitable sulphated carbohydrate under appropriate conditions to form filaments, and monitoring for the presence of filaments.

Tau protein and sulphated carbohydrate, ea sulphated glycosaminoglycan, will react under appropriate conditions to form filaments, either paired helical filaments or straight filaments. If filament formation is affected when the reaction is carried out in the presence of an agent being screened, this is possibly due to an interfering, inhibiting or blocking effect of the agent. An agent which inhibits assembly of PHFs in vitro may also have an inhibiting effect in vivo and thus have potential therapeutic value in delaying the dementing effects of Alzheimer's disease. The invention can thus provide a screen to identify agents worthy of further investigation for use in the treatment of Alzheimer's disease.

The tau protein may be the full length protein or a fragment thereof which forms filaments. Filament-forming fragments of tau generally include at least the portion thereof including three microtubule-binding repeats. Any of the 6 isoforms which occur in the adult human brain, as discussed above, may be used. The full length 3 repeat 381 amino acid isoform, which forms paired helical filaments very similar to the paired helical filaments found in the brain of patients with Alzheimer's disease as explained above, works very well and so is currently favoured. The tau protein may be modified in known manner by amino acid additions, substitutions and/or deletions that do not significantly affect filament formation. The term "tau protein" is used to cover all such proteins and fragments that form filaments under appropriate conditions.

The currently preferred sulphated carbohydrate is sulphated glycosaminoglycan, conveniently heparin or heparan sulphate.

The reaction may be carried out under physiological conditions, eg. by incubating the reagents in MOPS and AEBSF as described below, and provides quantitative results. Good results have been obtained by incubating with 30 mM MOPS. 1 mM AEBSF, pH 7.4 at 30° C., with filament formation starting after 5 h and reaching a maximum after 48 h. Tau concentration is suitably at least 40 $\mu$M, with a tau/sulphated glycosaminoglycan molar ratio of approximately 4:1 giving good results.

The presence (or otherwise) of filaments may be monitored by using electron microscopy or other appropriate methods.

The invention will be further described, by way of illustration, in the following examples and with reference to the accompanying figures in which:

FIG. 1 is a series of electron micrographs of sulphated glycosaminoglycan-induced filament assemblies formed from: the three repeat-containing 381 amino acid isoform of human tau (htau37) (FIG. 1A); the four repeat-containing 441 amino acid isoform of human tau (htau40) (FIG. 1B), and htau 37 phosphorylated with NCLK (FIG. 1C). The scale bar in FIG. 1C is 100 nm.

FIG. 2 is a series of electron micrographs of paired helical-like filaments marked with antibodies directed against the amino-terminus (antiserum 133) (FIG. 2A); the carboxy-terminus (antiserum 134) (FIG. 2B); and the microtubule-binding repeats (antiserum 135) (FIG. 2C) of human tau. The scale bar in FIG. 2C is 100 nm.

FIG. 3A shows an electrophoretic gel of aliquots eluted from a heparin-Sepharose column with buffer containing different concentrations of NaCl, and illustrates binding of tau proteins to heparin-Sepharose.

FIG. 3B is a graph of microtubule-bound tau (%) versus heparin (mg/ml) and illustrates the effects of heparin on the binding of tau to microtubules.

FIG. 3C is a graph of turbidity (at 350 nm) versus time, and illustrates the effect of addition of heparin (after 20 minutes incubation) on tau-promoted microtubule assembly.

Figure 4:
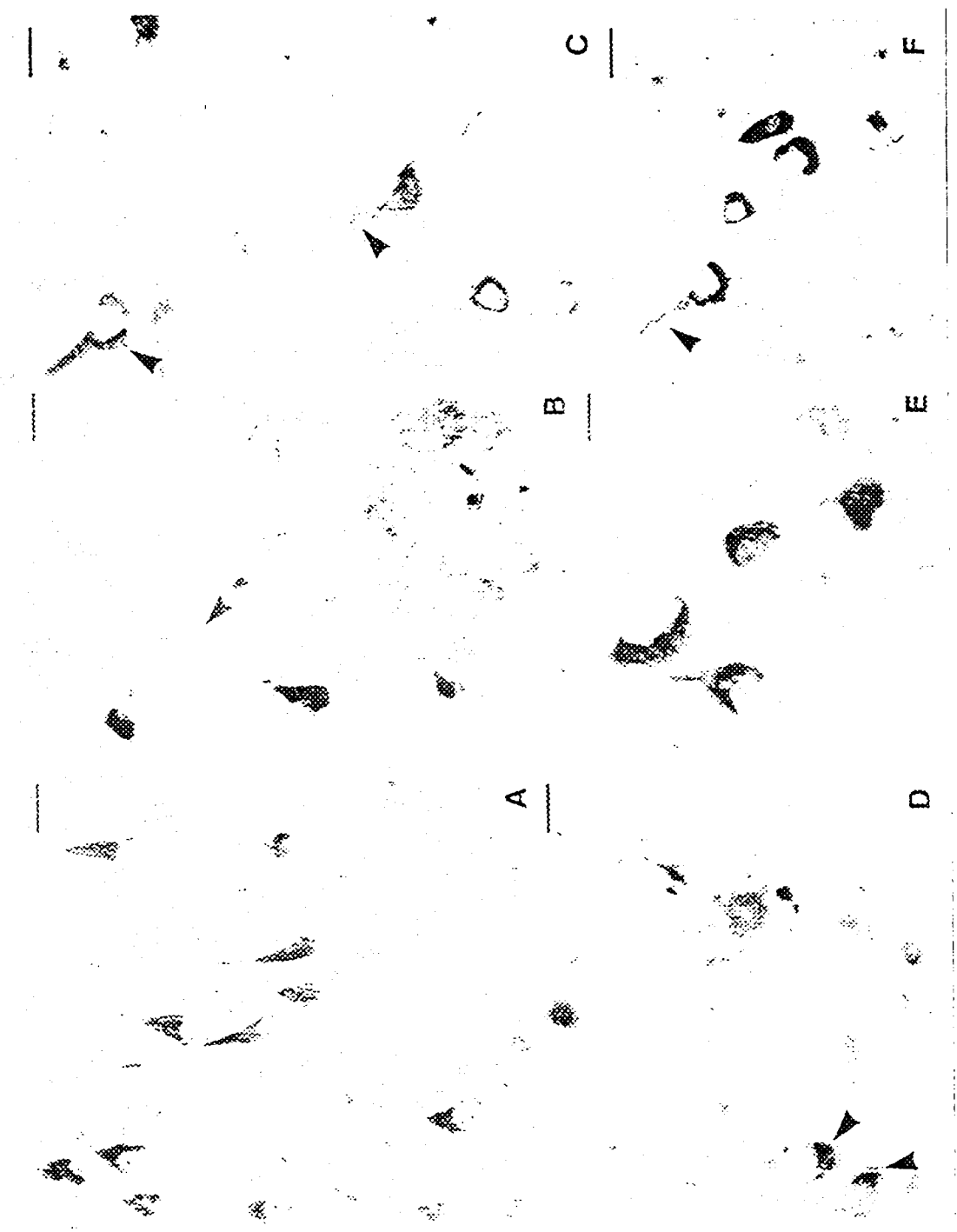

FIG. 4 is a series of photographs of tissue sections of hippocampal formation from Alzheimer's disease brain labelled with the anti-heparan sulphate antibody 10E4 stained in brown (photograph A) and double stained brain labelled with 10E4 and the phosphorylation-dependent anti-tau antibody AT8 stained in blue (photographs B–F). Scale bars: 45 $\mu$m in (A), 34 $\mu$m in (B), 30 $\mu$m in (C), 24 $\mu$m in (D) and (E). and 40 $\mu$m in (F).

EXAMPLE 1

Experiments were carried out using sulphated glycosaminoglycans to stimulate phosphorylation of tau.

Tau protein isoforms (the three repeat-containing 381 amino acid isoform of human tau (htau37) and the four repeat-containing 441 amino acid isoform of human tau (htau40)) were expressed in *E. coli*, as described (28). For tau purification, frozen pellets from 10 L bacterial culture were resuspended in 240 ml of 50 mM Tris, pH 7.4, 0.1 mM EDTA, 0.1 mM DTT, 0.1 mM phenylmethylsulphonyl fluoride (PMSF) (buffer A) and sonicated for 5×1 min on ice. Following centrifugation the supernatant was filtered through a DE-52 column (4×4 cm) and the flow-through fractions applied to a phosphocellulose column equilibrated in buffer A. After washing with buffer A containing 0.1 M NaCl, a 0.1 M–0.5 M NaCl gradient was applied and the tau-containing fractions concentrated by adding ammonium sulphate to 50%. The sediment was solubilised in 50 mM MES, pH 6.25, 0.1 mM DTT, 0.1 mM PMSF (buffer B) and applied to a S-200 column (1.3×100 cm) equilibrated in buffer B. Tau-containing fractions were applied to a Mono S column equilibrated in buffer B and eluted using a salt gradient. Peak fractions were concentrated by speed vacuum and dialysed against 40 mM Hepes, pH 7.4, 0.1 mM DWT, 0.1 mM PMSF. Tau purification was monitored by SDS-PAGE.

Purified htau37 and htau40 (80 $\mu$M) were incubated with heparin (20 $\mu$M, BDH) in 25 $\mu$l of 30 mM 3-[N-Morpholino] propane-sulphonic acid (MOPS), 1 mM [4-(2-aminoethyl) benzenesulphonylfluoride] (AEBSF, Calbiochem), pH 7.4, at 30° C. for 48 h. Aliquots were removed and examined by electron microscopy, as described (7). In some cases, htau37 was phosphorylated with 5U/ml recombinant neuronal cdc2-like kinase (NCLK) (29), prior to the addition of heparin. Results are shown in FIG. 1.

Figures 1A, 1B, 1C:
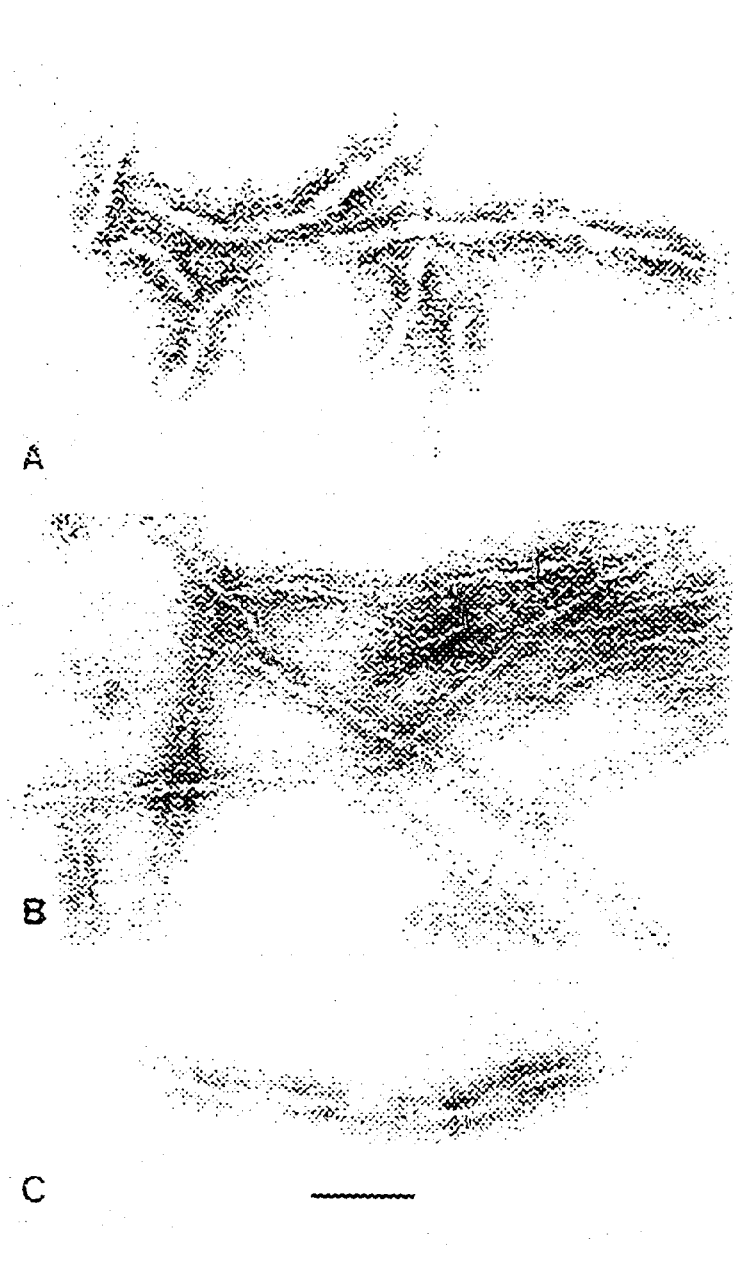

As shown in FIG. 1, electron microscopy revealed the presence of numerous filaments, with different morphologies for tau isoforms with three or four microtubule-binding repeats. Tau isoforms with three repeats gave filaments with a typical paired helical morphology (FIG. 1A), whereas tau isoforms with four repeats gave filaments with a straight appearance (FIG. 1B). Tau protein that had been phosphorylated by p42 mitogen-activated protein (MAP) kinase or NCLK prior to incubation with heparin (or heparan sulphate) formed filaments that were indistinguishable from those formed by non-phosphorylated tau, indicating that tau phosphorylation is neither stimulatory not inhibitory for in vitro filament formation (FIG. 1C). Filaments with the same morphology formed upon co-incubation of tau with sulphated glycosaminoglycans and p42 MAP kinase or NCLK.

At optimal tau and heparin concentrations, paired helical-like filaments started to form after approximately 5 h at 30° C. in 30 mM MOPS, 1 mM AEBSF, pH 7.4, reaching a maximum number after 48 h. Filament formation required a critical tau concentration, with the tau/sulphated glycosaminoglycan ratio being of crucial importance. Paired helical and straight filaments formed at tau concentrations above 40 $\mu$M, with a tau/sulphated glycosaminoglycan molar ratio of approximately 4:1. These characteristics suggest that filament formation is a nucleation-dependent process, by which the binding of tau to sulphated glycosaminoglycans leads to the formation of an ordered nucleus that allows growth of tau filaments to occur. The number of filaments, but not their morphology, correlated with the degree or glycosaminoglycan sulphation: the largest number was obtained following incubation of tau with heparin, with smaller numbers after incubation with heparan sulphate. Chondroitin sulphate and dermatan sulphate gave the smallest number of filaments, whereas hyaluronic acid gave no filaments. Similarly, no filaments were obtained following incubation of tau with poly-L-glutamic acid, indicating that filament formation does not result from a simple charge interaction.

No filaments were observed with tau protein on its own, either unphosphorylated or phosphorylated by MAP kinase or NCLK. Sulphated glycosaminoglycans on their own also failed to form filaments. Similar results were obtained in over 50 separate experiments using tau isoforms and heparan sulphate or heparin from different commercial sources, with the molecular masses of heparin ranging from 5–30 kDa.

The results thus demonstrate that tau forms filaments in a glycosaminoglycan-dependent, but phosphorylation-independent manner. Further, tau can form filaments in vitro under physiological conditions in quantitative manner.

Example 2

Recombinant htau37(80 $\mu$M) was incubated with heparin (20 $\mu$M) in 30 mM MOPS, 1 mM AEBSF, pH 7.4 at 30° C. for 48 h. Following a 1 h centrifugation at 346,000×g, the filament pellets were resuspended in 30 mM MOPS, 1 mM AEBSF, pH 7.4, and processed for immunoelectron microscopy, as described (7), using antibodies directed against the amino-terminus (antiserum 133), carboxy-terminus (antiserum 134) and microtubule-binding repeat region (antiserum 135) of tau.

Figure 2A:
Figure 2B:
Figure 2C:

Results are shown in FIG. 2. Gold labelling is seen with 133 and 134. but not with 135. Thus, the paired helical-like filaments were decorated by antibodies directed against the amino- and carboxy-termini of tau, but not by antibody against the microtubule-binding repeat region.

These results, which indicate that in the filaments the repeat region of tau is inaccessible to the antibody, are identical to those obtained previously with PHFs from Alzheimer's disease brain (7), thus demonstrating a similar organisation of the tau molecule in the two types of filament. In the presence of heparin, each of the six recombinant human brain tau isoforms formed either paired helical or straight filaments. Similar results were obtained with tau proteins consisting of only three or four microtubule-binding repeats and with proteins comprising the repeat region and the carboxy-terminus of tau. By contrast, a protein consisting of the amino-terminal half of tau up to but excluding the repeat region failed to give filaments (data not shown).

These findings establish that the microtubule-binding repeat region of tau is essential for sulphated glycosaminoglycan-induced filament formation. It is well known that three microtubule-binding repeats of tau form the core of the PHF from Alzheimer's disease brain (4, 15), thus supporting the evidence for a similar organisation of the two types of filament. The dimensions of tau filaments formed in the presence of sulphated glycosaminoglycans were similar to those of filaments from Alzheimer's disease brain, with a diameter of approximately 20 nm for twisted and 15 nm for straight filaments and a crossing-over spacing of approximately 80 nm for paired helical-like filaments, though their twist was in general less regular than in Alzheimer filaments.

Example 3

The heparin-binding properties of tau were investigated following incubation with heparin-Sepharose.

Sixty µg of an equal mixture of the six recombinant human brain tau isoforms or 20 µg bovine brain tubuiln (Cytoskeleton. Inc.) were applied to a 4.5×8 mm heparin-Sepharose (Pharmacia) column in 30 mM MOPS, pH 7.4. Elution was carried out with 10 column volumes of buffer containing 0 (flow-through, f.t.), 0.15 M, 0.3 M, 0.5 M and 1.0 M NaCl. Aliquots were subjected to SDS-PAGE and stained with Coomassie blue. Results are shown in FIG. 3A. This shows that the six recombinant tau isoforms bound to heparin-Sepharose in a salt-dependent manner, eluting at 0.3–0.5 M NaCl.

Tau protein consisting of only three or four repeats or comprising the repeat region and the carboxy-terminus also bound to heparin-Sepharose, as did a protein consisting of the amino-terminal half of tau up to but excluding the repeat region (data not shown). This demonstrates the presence of multiple heparin-binding sites that are distributed throughout the tau sequence. Similarly, recombinant tau phosphorylated with p42 MAP kinase or NCLK was able to bind to heparin-Sepharose, indicating that phosphorylation did not significantly interfere with the ability of tau to bind to heparin. This binding is probably mediated through electrostatic interactions between the negative charges in heparin and positive charges in tau. Tau is positively charged in the repeat region and in the region upstream of the repeats, whereas the amino-terminal 125 amino acids are negatively charged.

Experiments were then carried out to examine the influence of heparin on the ability to tau to bind to microtubules and to promote microtubule assembly.

Tublin was assembled into microtubules by incubation with 20 µM taxol (Calbiochem) in assembly buffer (80 mM PIPES, 1 mM $MgCl_2$, 1 mM EGTA, 1 mM DTT. 1 mM GTP, pH 6.8) for 15 min at 37° C. Recombinant htau40 (4 µM. 0.18 mg/ml) was incubated with different concentrations of heparin (0, 2, 20, 100, 200, 500, 1000, 2000 µg/ml) in assembly buffer for 10 min at 37° C. added to 10 µM taxol-stabilised microtubules and incubated for a further 20 min. The suspensions were layered onto a buffered cushion consisting of assembly buffer containing 25% glycerol and 20 µM taxol and centrifuged for 20 min at 346,000×g. The resulting pellets were resuspended in the same volume of buffer as that of the supernatant. Aliquots of supernatants (free tau) and pellets (microtubule-bound tau) were subjected to SDS-PAGE and stained with Coomassie blue. Protein concentrations were estimated by scanning the gels with a Moleculate Dynamics computing densitometer (Model 300A). They are expressed as % of tau bound to microtubules in the absence of heparin (taken as 100%).

Results are shown in FIG. 3B, which demonstrates that the presence of heparin prevented tau from binding to taxol-stabilised microtubules.

To investigate the effects of heparin on tau-promoted microtubule assembly, recombinant htau40 (2 µM) was incubated with tubulin (10 µM) in assembly buffer at 37° C. After 20 min heparin (10 µM) was added and the incubation continued for a further 20 min. Polymerisation and depolymerisation of microtubules were monitored by measuring the turbidity at 350 nm. Results are shown in FIG. 3C, which demonstrates that microtubules assembled in the presence of tau rapidly depolymerised upon addition of heparin. Microtubules assembled from concentrated tubulin without tau did not disassemble when heparin was added (data not shown). These results demonstrate that heparin prevent tau from binding to microtubules and from promoting microtubule assembly and stability.

Example 4

Previous experiments have shown the presence in Alzheimer's disease of heparan sulphate within nerve cells with neurofibrillary lesions (16–19). However, it had not been investigated whether heparan sulphate and hyperphosphorylated tau co-exist in the earliest known stages of neurofibrillary pathology, which consist of nerve cells staining diffusely with phosphorylation-dependent anti-tau antibodies ("pre-tangle" stage of Alzheimer's disease) (11). Single- and double-labelling immunohistochemistry were therefore performed on hippocampal formation from Alzheimer's disease brain using the anti-heparan sulphate antibody 10E4 (20) and the phosphorylation-dependent anti-tau antibody AT8 (21, 22).

Deparaffinised 4 µm sections through the hippocampal formation from three Alzheimer's disease patients (76, 79 and 80 years of age) were used for single and double-labelling immunohistochemistry, using a modification of the previously described procedure (30). Antibody 10E4 (Seikagaku Corporation) was used at 1:250 and antibody AT8 (Innogenetics) at 1:500. Tissue sections were incubated overnight at 4° C. with the first or second primary antibody in 50 mM Tris/HCl, pH 7.4, containing 0.2% Tween-20 and 150 mM NaCl. The sections were washed in phosphate-buffered saline (PBS) and incubated for 2 h at room temperature with biotinylated horse anti-mouse IgG or goat anti-mouse IgM (Vector) diluted 1:200. After a further was in PBS they were incubated for 1 h with avidin-DH (Vector) diluted 1:100 and the staining developed with 3,3-diaminobenzidine. The sections were then washed in PBS, counterstained with 0.01% thionin, dehydrated and mounted in DPX. For double-labelling, to avoid non-specific staining, sections were incubated with avidin-biotin (Vector Blocking kit) after the first staining. Following washing in PBS, they were incubated overnight at 4° C. with the second primary antibody and the above procedure repeated, using 4-chloro-1-naphthol as the substrate. Double-stained sections were directly mounted in gelatin. In some experiments, the order of the primary antibodies was inverted and the first or second primary antibody omitted. Furthermore, tissue sections were incubated for 3 h at 37° C. with 0, 2.5, 5 or 10 mU heparitinase (Seikagaku Corporation) in 0.5 ml 50 mM Hepes, pH 7.0, containing 100 mM NaCl, 1 mM $CaCl_2$, 10 µg/ml bovine serum albumin and 1 mM PMSF. Following washing in PBS. the sections were incubated with antibody 10E4, as described above. Staining with 10E4 was greatly reduced with 2.5 mU heparitinase and abolished with 5 and 10 mU of the enzyme, whereas AT8 staining was unaffected by heparitinase treatment. AT8 staining was abolished following incubation of the diluted antibody with 10 μM phosphorylated recombinant tau protein.

Results are shown in FIG. 4. 10E4 staining was in brown (lighter patches in the Figure) and AT8 staining in blue (darker patches in the Figure) (Nomarski optics). The section in (A) was counterstained with thionin, with no counterstaining in (B–F).

As shown in FIG. 4A. a subset of pyramidal cells was strongly immunoreactive with 10E4: these included cells with overt neurofibrillary tangles, as well as non-tangle-bearing cells. Double-labelling immunohistochemistry showed that nerve cells that stained diffusely with AT8 also stained with 10E4 (FIGS. 4B–F). In FIGS. 4B–F, in most stained cells, the brown 10E4 and the blue AT8 staining were inter-mixed due to full double-labelling. However, in some nerve cells, the heparan sulphate staining was more extensive than the tau staining: pyramidal cells that are partially double-labelled are arrowed in FIGS. 4 C, D and F. In particular, small patches of tau staining were observed in some pyramidal cells with diffuse heparan sulphate staining (arrowed cells in FIG. 4D). Moreover, some tau-negative nerve cells were heparan sulphate-positive, suggesting that heparan sulphate staining may precede staining for hyperphosphorylated tau. As shown previously (16–19), tau and heparan sulphate immunoreactivities co-existed in nerve cells with overt neurofibrillary lesions and amyloid plaques were stained with heparan sulphate antibody. The immunostaining was specific, as the heparan sulphate staining was absent following heparitinase treatment of the tissue sections and the tau staining was absent following pre-adsorption of the antibody with phosphorylated tau. In age-matched control brains only very small numbers of cells stained with 10E4 or AT8. This shows that heparan sulphate and hyperphosphorylated tau co-exist in nerve cells of the Alzheimer's disease brain at the earliest known stages of neurofibrillary pathology.

Taken together, the present findings indicate that an interaction between tau protein and sulphated glycosaminoglycans may lead to the formation of the neurofibrillary lesions of Alzheimer's disease. The latter consist of PHFs containing hyperphosphorylated tau protein that is unable to bind to microtubules (3–6, 9, 10). Sulphated glycosaminoglycans are known to stimulate tau phosphorylation by a number of protein kinases in a substrate-dependent manner (12–14). We show here that a phosphorylation-independent interaction between full-length tau and sulphated glycosaminoglycans leads to the formation of filaments closely resembling those found in the Alzheimer's disease brain. In addition to PHFs, the latter consist of a small number of biochemically and structurally related straight filaments (23). In the presence of sulphated glycosaminoglycans, three repeat-containing tau isoforms gave rise to paired helical-like filaments, whereas four repeat isoforms formed straight filaments, thus suggesting a mechanism for the two tau assemblies of Alzheimer's disease. Previous studies under non-physiological conditions have shown the formation of paired helical-like filaments from three microtubule-binding repeats of tau (24–26) and to a very limited extent from the full-length molecule (27). The results presented here suggest that filament formation resulting from the binding of tau to sulphated glycosaminoglycans is a nucleation-dependent process that allows full-length tau to assemble through three microtubule-binding repeats to form the PHF. It is also shown that this interaction prevents tau from binding to microtubules and from promoting microtubule assembly. Moreover, heparan sulphate and tau immunoreactivities were found to co-localise in nerve cells in Alzheimer's disease brain prior to the formation of overt neurofibrillary lesions. These results suggest that an increase in sulphated glycosaminoglycans within the cytoplasm of nerve cells may trigger the hyperphosphorylation of tau, destabilise microtubules and induce assembly of PHFs, thus resulting in the neurofibrillary pathology of Alzheimer's disease. They also provide a simple assay for the identification of compounds that interfere with PHF formation.

REFERENCES

1. Goedert, M. Trends Neurosci. 16, 460–465 (1993)
2. Lee, V. M. -Y. Curr. Opin. Neurobiol. 5, 663–668 (1995).
3. Goedert, M., Wischik. C. M., Crowther, R. A., Walker, J. E. & Klug, A. Proc. Natl. Acad. Sci. USA 85, 4051–4055 (1988).
4. Wischik, C. M. et al. Proc. Natl. Acad. Sci. USA 85, 4506–4510 (1988).
5. Kondo, J. et al. Neuron 1, 827–834 (1988).
6. Lee. V. M. -Y., Balin. B. J., Otvos. L. & Trojanowski, J. Q. Science 251, 675–678 (1991)
7. Goedert, A. Spillantini. M. G. Cairns, N. J. & Crowther R. A. Neuron 8, 159–168 (1992).
8. Greenberg, S. C., Davies, P., Schein, J. D. & Binder, L. I. J. biol. Chem. 267, 564–569 (1992).
9. Bramblett, G. T. et al. Neuron 10, 1089–1099 (1993).
10. Yoshida, H. & Ihara, Y. J. Neurochem. 61, 1183–1186 (1993).
11. Braak, E., Braak, H. & Mandelkow, E. M. Acta Neuropathol. 87, 554–567 (1994).
12. Mawal-Dewan, M., Sen, P. C., Abdel-Ghany, M., Shalloway, D. & Racker, E. J. biol Chem. 267, 19705–19709 (1992).
13. Brandt, R., Lee, G., Teplow, D. B. Shalloway, D. & Abdel-Ghany, M. J. biol. Chem 269, 11176–11782 (1994).
14. Yana, S. -D. Yu, J. -S. Shiah, S. -G. & Huang, J. J. J. Neurochem. 63, 1416–1425 (1994).
15. Jakes, R., Novak, M., Davison, M. & Wischik, C. M. EMBO J. 10, 2725–2729 (1991).
16. Snow, A. D., Lara, S. Nochlin, D. & Wight, T. N. Acta Neuropathol. 78, 113–123 (1989).
17. Snow, A. D. et al. Am. J. Pathol. 137, 1253–1573 (1990).
18. Perry, G. et al. J. Neurosci. 11, 3679–3683 (1991).
19. Kato, T. et al. Neurosci. Lett. 122, 33–36 (1991).
20. David, G. Bai, X. M., van der Schueren, B., Cassiman, J. -J. & van den Berghe, H. J. Cell Biol. 119, 961–975 (1992).
21. Mercken, M. et al. Acta Neuropathol. 84, 265–272 (1992).
22. Goedert, M., Jakes, R. & Vanmechelen E. Neurosci. Lett. 189, 167–170 (1995).
23. Crowther, R. A. Proc. Natl. Acad. Sci. USA. 88, 2288–2292 (1991).
24. Wille, H., Drewes, G., Biernat, J., Mandelkow, E. M. & Mandelkow, E. J. Cell Biol. 118, 573–584 (1992).
25. Crowther, R. A., Olesen, O. F., Jakes, R. & Goedert, M. FEBS Lett. 309, 199–202 (1992).
26. Schweers, O., Mandelkow, W. M., Biernat, J. & Mandlekow, E. Proc. Natl. Acad. Sci. USA 92, 8463–8467 (1995).
27. Crowther, R. A., Olesen, O. F., Smith, M. J., Jakes, R. & Goedert, M. (1994) FEBS Lett. 337, 135–138 (1994).
28. Goedert, M & Jakes, R. EMBO J. 9, 4225–4230 (1990).
29. Hasegawa, M. et al. FEBS Lett. 384, 25–30 (1996).
30. Spillantini, M. G., Goedert, M. Jakes, R. & Klug, A. Proc. Natl. Acad. Sci. USA 87, 3947–3951 (1990).
31. Crowther, R. A. Current Opinion in Structural Biology 3, 202–206 (1993).
32. Goedert, M. et al. Neurobiology of Ageing 16(3), 325–334 (1995).

What is claimed is:

1. A method of screening an agent for potential use in the treatment of Alzheimer's disease, comprising reacting, in the presence of the agent, tau protein with a suitable sulphated carbohydrate under appropriate conditions to form filaments, and monitoring for the presence of filaments.

2. A method according to claim 1, wherein the tau protein comprises the full length 3 repeat 381 amino acid isoform.

3. A method according to claim 1 or 2, wherein the sulphated carbohydrate is a sulphated glycosaminoglycan.

4. A method according to claim 3, wherein the sulphated glycosaminoglycan is heparin or heparan sulphate.

5. A method according to claim 1, wherein the reaction is carried out under physiological conditions.

6. A method according to claim 5, wherein the reaction is carried out by incubating the reagents in MOPS and AEBSF.

7. A method according to claim 1, wherein the presence of filaments is monitored by using electron microscopy or other appropriate methods.

* * * * *

UNITED STATES PATENT AND TRADEMARK OFFICE
CERTIFICATE OF CORRECTION

PATENT NO. : 6,245,575 B1
DATED : June 12, 2001
INVENTOR(S) : Goedert et al.

Page 1 of 1

It is certified that error appears in the above-identified patent and that said Letters Patent is hereby corrected as shown below:

Claim 1,
Should read as follows: -- A method of screening an agent that inhibits formation of filaments of tau protein, comprising reacting, in the presence of the agent, isolated tau protein with a suitable sulphated carbohydrate under appropriate conditions to form filaments, and monitoring for the formation of filaments, wherein a decrease of absence of filaments as compared to tau protein with a suitable sulphated carbohydrate under appropriate conditions to form filaments without the agent, indicates the usefulness of the agent for inhibiting formation of filaments of tau protein. --

Claim 7,
Lines 2-3, delete "or other appropriate methods".

Signed and Sealed this

Ninth Day of April, 2002

Attest:

JAMES E. ROGAN
Attesting Officer
Director of the United States Patent and Trademark Office